United States Patent [19]
Müller et al.

[11] Patent Number: 6,153,761
[45] Date of Patent: Nov. 28, 2000

[54] SULPHONYLAMINOCARBONYLTRIA-ZOLINONES HAVING HALOGENOALKYLTHIO SUBSTITUENTS

[75] Inventors: Klaus-Helmut Müller, Düsseldorf; Rolf Kirsten, Monheim; Ernst Rudolf F. Gesing, Erkrath-Hochdahl; Joachim Kluth, Langenfeld; Kurt Findeisen, Leverkusen; Johannes R. Jansen, Monheim; Klaus König, Odenthal; Hans-Jochem Riebel, Wuppertal; Dietmar Bielefeldt, Ratingen; Markus Dollinger; Hans-Joachim Santel, both of Leverkusen; Klaus Stenzel, Düsseldorf, all of Germany

[73] Assignee: Bayer Aktiengesellschaft, Leverkusen, Germany

[21] Appl. No.: 09/368,379

[22] Filed: Aug. 4, 1999

Related U.S. Application Data

[62] Division of application No. 08/894,932, filed as application No. PCT/EP96/00834, Mar. 1, 1996, Pat. No. 5,994,273.

[30] Foreign Application Priority Data

Aug. 3, 1995 [DE] Germany .................... 198 08 119

[51] Int. Cl.⁷ .................................................. C07D 249/12
[52] U.S. Cl. ............................................................ 548/263.6
[58] Field of Search ................................................ 548/263.6

[56] References Cited

U.S. PATENT DOCUMENTS

| | | |
|---|---|---|
| 4,098,896 | 7/1978 | Edwards . |
| 5,057,144 | 10/1991 | Daum et al. . |
| 5,085,684 | 2/1992 | Müller et al. . |

FOREIGN PATENT DOCUMENTS

| | | |
|---|---|---|
| 0 341 489 A1 | 11/1989 | European Pat. Off. . |
| 2 412 564 | 10/1974 | Germany . |
| 39 36 623 A1 | 5/1991 | Germany . |

OTHER PUBLICATIONS

Heterocycles, 82:16845h (1975) p. 503: Abstract of Ger.Offen. 2,412,564.
Cram and Hammond, "Organic Chemistry," McGraw–Hill Book Co., NY (1964) 2nd ed. pp. 565–567.

*Primary Examiner*—Patricia L. Morris
*Attorney, Agent, or Firm*—Norris, McLaughlin & Marcus, P.A.

[57] ABSTRACT

The invention relates to novel sulphonylaminocarbonyltriazolinones of the formula (I),

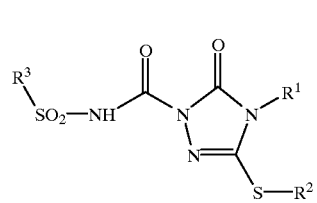

in which
$R^1$ represents hydrogen, hydroxyl, amino, alkylideneamino or a respectively optionally substituted radical from the group consisting of alkyl, alkenyl, alkinyl, alkylamino, dialkylamino, alkanoylamino, cycloalkyl, cycloalkylalkyl, cycloalkylamino, aryl, arylalkyl,
$R^2$ represents respectively halogen-substituted alkyl or alkenyl and
$R^3$ represents a respectively optionally substituted radical from the group consisting of alkyl, aralkyl, aryl, heteroaryl,
and to salts of compounds of the formula (I), to processes and novel intermediates for preparing the compounds (I) and to their use as herbicides and/or fungicides.

1 Claim, No Drawings

SULPHONYLAMINOCARBONYLTRIA-ZOLINONES HAVING HALOGENOALKYLTHIO SUBSTITUENTS

This application is a divisional of application Ser. No. 08/894,932, filed on Nov. 17, 1997, now U.S. Pat. No. 5,994,273, issued Nov. 30, 1999, which is a 371 of PCT/EP96/00834, filed on Mar. 1, 1996.

The invention relates to novel sulphonylaminocarbonyl-triazolinones having halogenoalkylthio substituents, to a plurality of processes and novel intermediates for their preparation and to their use as herbicides and fungicides.

Certain sulphonylaminocarbonyltriazolinones are already known to have herbicidal properties (cf. EP-A 34148, EP-A 422469, EP-A 425948, EP-A 431291, EP-A 507171). However, the activity of these compounds is not in all aspects satisfactory.

This invention accordingly provides the novel sulphonylaminocarbonyltriazolinones having halogenoalkylthio substituents of the general formula (I)

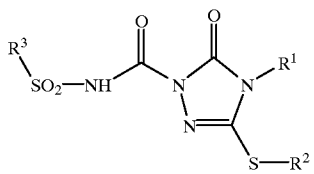
(I)

in which
R$^1$ represents hydrogen, hydroxyl, amino, alkylidene-amino or a respectively optionally substituted radical from the group consisting of alkyl, alkenyl, alkinyl, alkylamino, dialkylamino, alkanoylamino, cycloalkyl, cycloalkylalkyl, cycloalkylamino, aryl, arylalkyl,
R$^2$ represents respectively halogen-substituted alkyl or alkenyl and
R$^3$ represents a respectively optionally substituted radical from the group consisting of alkyl, aralkyl, aryl, heteroaryl,
and salts of compounds of the formula (I).

The novel sulphonylaminocarbonyltriazolinones having halogenoalkylthio substituents of the general formula (I) are obtained when
(a) triazolinones of the general formula (II)

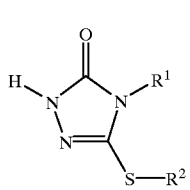
(II)

in which
R$^1$ and R$^2$ are each as defined above
are reacted with sulphonyl isocyanates of the general formula (III)

$$R^3—SO_2—N=C=O \quad (III)$$

in which
R$^3$ is as defined above,
if appropriate in the presence of a reaction auxiliary and if appropriate in the presence of a diluent, or (b) triazolinone derivatives of the general formula (IV)

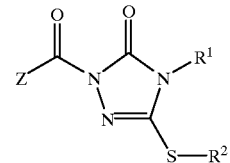
(IV)

in which
R$^1$ and R$^2$ are each as defined above and
Z represents halogen, alkoxy, aralkoxy or aryloxy are reacted with sulphonamides of the general formula (V)

$$R^3—SO_2—NH_2 \quad (V)$$

in which
R$^3$ is as defined above,
if appropriate in the presence of an acid acceptor and if appropriate in the presence of a diluent, or
(c) triazolinones of the general formula (II)

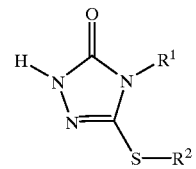
(II)

in which
R$^1$ and R$^2$ are each as defined above
are reacted with sulphonamide derivatives of the general formula (VI)

$$R^3—SO_2—NH—CO—Z \quad (VI)$$

in which
R$^3$ is as defined above and
Z represents halogen, alkoxy, aralkoxy or aryloxy,
if appropriate in the presence of an acid acceptor and if appropriate in the presence of a diluent, or
(d) triazolinones of the general formula (II)

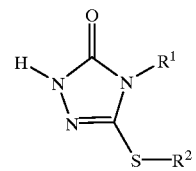
(II)

in which
R$^1$ and R$^2$ are each as defined above
are reacted with sulphonyl halides of the general formula (VII)

$$R^3—SO_2—X \quad (VII)$$

in which
R$^3$ is as defined above and
X represents halogen and metal cyanates of the general formula (VIII)

$$MOCN \quad (VIII)$$

in which

M represents an alkali metal or an alkaline earth metal equivalent, if appropriate in the presence of a reaction auxiliary and if appropriate in the presence of a diluent, and the compounds of the formula (I) obtained by process (a), (b), (c) or (d) are, if required, converted by customary methods into salts.

The novel sulphonylaminocarbonyltriazolinones having halogenoalkylthio substituents of the general formula (I) have strong herbicidal and/or fungicidal activity.

The invention preferably provides compounds of formula (I) in which $R^1$ represents hydrogen, hydroxyl, amino, $C_1$–$C_6$-alkylideneamino, or optionally fluorine-, chlorine-, bromine-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, or respectively optionally fluorine-, chlorine- and/or bromine-substituted $C_2$–$C_6$-alkenyl or $C_2$–$C_6$-alkinyl, or respectively optionally fluorine- and/or chlorine-substituted $C_1$–$C_6$-alkylamino, di-($C_1$–$C_4$-alkyl)-amino or $C_1$–$C_4$-alkanoylamino, or respectively optionally fluorine-, chlorine-, bromine- and/or $C_1$–$C_4$-alkyl-substituted $C_3$–$C_6$-cycloalkyl or $C_3$–$C_6$-cycloalkyl-$C_1$–$C_4$-alkyl, or respectively optionally fluorine-, chlorine-, bromine-, cyano-, nitro-, $C_1$–$C_4$-alkyl-, trifluoromethyl-, $C_1$–$C_4$-alkoxy- and/or $C_1$–$C_4$-alkoxy-carbonyl-substituted phenyl or phenyl-$C_1$–$C_4$-alkyl, $R^2$ represents respectively fluorine-, chlorine- and/or bromine-substituted $C_1$–$C_6$-alkyl or $C_2$–$C_6$-alkenyl and $R^3$ represents the grouping

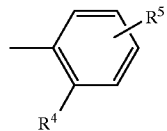

in which $R^4$ and $R^5$ are identical or different and each represent hydrogen, fluorine, chlorine, bromine, iodine, nitro, $C_1$–$C_6$-alkyl, (which is optionally substituted by fluorine, chlorine, bromine, cyano, carboxyl, $C_1$–$C_4$-alkoxy-carbonyl, $C_1$–$C_4$-alkylamino-carbonyl, di-($C_1$–$C_4$-alkyl)amino-carbonyl, hydroxyl, $C_1$–$C_4$-alkoxy, formyloxy, $C_1$–$C_4$-alkylcarbonyloxy, $C_1$–$C_4$-alkoxy-carbonyloxy, $C_1$–$C_4$-alkylamino-carbonyloxy, $C_1$–$C_4$-alkylthio, $C_1$–$C_4$-alkylsulphinyl, $C_1$–$C_4$-alkyl-sulphonyl, di-($C_1$–$C_4$-alkyl)-aminosulphonyl, $C_3$–$C_6$-cycloalkyl or phenyl), or $C_2$–$C_6$-alkenyl (which is optionally substituted by fluorine, chlorine, bromine, cyano, $C_1$–$C_4$-alkoxycarbonyl, carboxyl or phenyl), or $C_2$–$C_6$-alkinyl (which is optionally substituted by fluorine, chlorine, bromine, cyano, $C_1$–$C_4$-alkoxy-carbonyl, carboxyl or phenyl), or $C_1$–$C_4$-alkoxy (which is optionally substituted by fluorine, chlorine, bromine, cyano, carboxyl, $C_1$–$C_4$-alkoxy-carbonyl, $C_1$–$C_4$-alkoxy, $C_1$–$C_4$-alkylthio, $C_1$–$C_4$-alkylsulphinyl or $C_1$–$C_4$-alkylsulphonyl), or $C_1$–$C_4$-alkylthio (which is optionally substituted by fluorine, chlorine, bromine, cyano, carboxyl, $C_1$–$C_4$-alkoxy-carbonyl, $C_1$–$C_4$-alkylthio, $C_1$–$C_4$-alkylsulphinyl or $C_1$–$C_4$-alkylsulphonyl), or $C_2$–$C_6$-alkenyloxy (which is optionally substituted by fluorine, chlorine, bromine, cyano or $C_1$–$C_4$-alkoxy-carbonyl), or $C_2$–$C_6$-alkenylthio (which is optionally substituted by fluorine, chlorine, bromine, cyano, nitro, $C_1$–$C_3$-alkylthio or $C_1$–$C_4$-alkoxycarbonyl), $C_3$–$C_6$-alkinyloxy, $C_3$–$C_6$-alkinylthio or the radical —$S(O)_p$—$R^6$, where p represents the numbers 1 or 2 and $R^6$ represents $C_1$–$C_4$-alkyl (which is optionally substituted by fluorine, chlorine, bromine, cyano or $C_1$–$C_4$-alkoxy-carbonyl), $C_3$–$C_6$-alkenyl, $C_3$–$C_6$-alkinyl, $C_1$–$C_4$-alkoxy, $C_1$–$C_4$-alkoxy-$C_1$–$C_4$-alkylamino, $C_1$–$C_4$-alkylamino, di-($C_1$–$C_4$-alkyl)-amino, phenyl or the radical —$NHOR^7$, where $R^7$ represents $C_1$–$C_{12}$-alkyl (which is optionally substituted by fluorine, chlorine, cyano, $C_1$–$C_4$-alkoxy, $C_1$–$C_4$-alkylthio, $C_1$–$C_4$-alkcylsulphinyl, $C_1$–$C_4$-alkylsulphonyl, $C_1$–$C_4$-alkyl-carbonyl, $C_1$–$C_4$-alkoxy-carbonyl, $C_1$–$C_4$-alkylamino-carbonyl or di-($C_1$–$C_4$-alkyl)-amino-carbonyl), or $C_3$–$C_6$-alkenyl (which is optionally substituted by fluorine, chlorine or bromine), $C_3$–$C_6$-alkinyl, $C_3$–$C_6$-cycloalkyl, $C_3$–$C_6$-cycloalkyl-$C_1$–$C_2$-alkyl, phenyl-$C_1$–$C_2$-alkyl (which is optionally substituted by fluorine, chlorine, nitro, cyano, $C_1$–$C_4$-alkyl, $C_1$–$C_4$-alkoxy or $C_1$–$C_4$-alkoxy-carbonyl), or benzohydryl or phenyl (which is optionally substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxy-carbonyl), $R^4$ and/or $R^5$ farther each represent phenyl or phenoxy, or $C_1$–$C_4$-alkyl-carbonylamino, $C_1$–$C_4$-alkoxy-carbonylamino, $C_1$–$C_4$-alkylamino-carbonyl-amino, di-($C_1$–$C_4$-alkyl)-amino-carbonylamino, or the radical —CO—$R^8$, where $R^8$ represents hydrogen, $C_1$–$C_6$-alkyl, $C_3$–$C_6$-cycloalkyl, $C_1$–$C_6$-alkoxy, $C_3$–$C_6$-cycloalkoxy, $C_3$–$C_6$-alkenyloxy, $C_1$–$C_4$-alkylthio, $C_1$–$C_4$-alkylamino, $C_1$–$C_4$-alkoxyamino, $C_1$–$C_4$-alkoxy-$C_1$–$C_4$-alkyl-amino or di-($C_1$–$C_4$-alkyl)-amino (each of which are optionally substituted by fluorine and/or chlorine), $R^4$ and/or $R^5$ further each represent trimethylsilyl, thiazolinyl, $C_1$–$C_4$-alkylsulphonyloxy, di-($C_1$–$C_4$-alkyl)-amino-sulphonylamino or the radical —CH=N—$R^9$, where $R^9$ represents optionally fluorine-, chlorine-, cyano-, carboxyl-, $C_1$–$C_4$-alkoxy-, $C_1$–$C_4$-alkylthio-, $C_1$–$C_4$-alkylsulphinyl- or $C_1$–$C_4$-alkylsulphonyl-substituted $C_1$–$C_6$-alkyl, or optionally fluorine- or chlorine-substituted benzyl, or optionally fluorine- or chlorine-substituted $C_3$–$C_6$-alkenyl or $C_3$–$C_6$-alkinyl, or optionally fluorine-, chlorine-, bromine-, $C_1$–$C_4$-alkyl-, $C_1$–$C_4$-alkoxy-, trifluoromethyl-, trifluoromethoxy- or trifluoro-methylthio-substituted phenyl, or optionally fluorine- and/or chlorine-substituted $C_1$–$C_6$-alkoxy, $C_3$–$C_6$-alkenoxy, $C_3$–$C_6$-alkinoxy or benzyloxy, or amino, $C_1$–$C_4$-alkylamino, di-($C_1$–$C_4$-alkyl)-amino, phenylamino, $C_1$–$C_4$-alkyl-carbonyl-amino, $C_1$–$C_4$-alkoxy-carbonylamino, $C_1$–$C_4$-alkyl- sulphonylamino or optionally fluorine-, chlorine-, bromine- or methyl-substituted phenylsulphonylamino, furthermore $R^3$ represents the radical

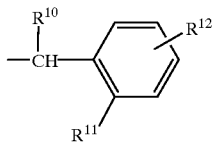

in which
$R^{10}$ represents hydrogen or $C_1$–$C_4$-alkyl,
$R^{11}$ and $R^{12}$ are identical or different and each represent hydrogen, fluorine, chlorine, bromine, nitro, cyano, $C_1$–$C_4$-alkyl (which is optionally substituted by fluorine and/or chlorine), $C_1$–$C_4$-alkoxy (which is optionally substituted by fluorine and/or chlorine), carboxyl, $C_1$–$C_4$-alkoxy-carbonyl, dimethylaminocarbonyl, $C_1$–$C_4$-alkylsulphonyl or di-($C_1$–$C_4$-alkyl)-aminosulphonyl;

furthermore $R^3$ represents the radical

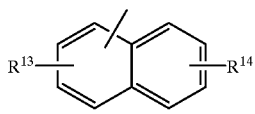

in which
$R^{13}$ and $R^{14}$ are identical or different and each represent hydrogen, fluorine, chlorine, bromine, nitro, cyano, $C_1$–$C_4$-alkyl (which is optionally substituted by fluorine and/or chlorine) or $C_1$–$C_4$-alkoxy (which is optionally substituted by fluorine and/or chlorine);

furthermore $R^3$ represents the radical

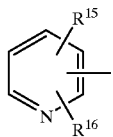

in which
$R^{15}$ and $R^{16}$ are identical or different and each represent hydrogen, fluorine, chlorine, bromine, nitro, cyano, $C_1$–$C_4$-alkyl (which is optionally substituted by fluorine and/or chlorine), $C_1$–$C_4$-alkoxy (which is optionally substituted by fluorine and/or chlorine), or $C_1$–$C_4$-alkylthio, $C_1$–$C_4$-alkylsulphinyl or $C_1$–$C_4$-alkylsulphonyl (which is optionally substituted by fluorine and/or chlorine), or aminosulphonyl, mono-($C_1$–$C_4$-alkyl)-aminosulphonyl, or di-($C_1$–$C_4$-alkyl)-aminosulphonyl or $C_1$–$C_4$-alkoxy-carbonyl or dimethylaminocarbonyl;

furthermore $R^3$ represents the radical

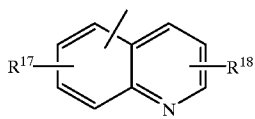

in which
$R^{17}$ and $R^{18}$ are identical or different and each represent hydrogen, fluorine, chlorine, bromine, $C_1$–$C_4$-alkyl (which is optionally substituted by fluorine and/or bromine), $C_1$–$C_4$-alkoxy (which is optionally substituted by fluorine and/or chlorine), or $C_1$–$C_4$-alkylthio, $C_1$–$C_4$-alkylsulphinyl or $C_1$–$C_4$-alkylsulphonyl (each of which are optionally substituted by fluorine and/or chlorine), or di-($C_1$–$C_4$-alkyl)-aminosulphonyl;

furthermore $R^3$ represents the radical

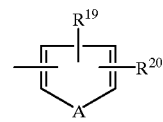

in which
$R^{19}$ and $R^{20}$ are identical or different and each represent hydrogen, fluorine, chlorine, bromine, cyano, nitro, $C_1$–$C_4$-alkyl (which is optionally substituted by fluorine and/or chlorine), $C_1$–$C_4$-alkoxy (which is optionally substituted by fluorine and/or chlorine), $C_1$–$C_4$-alkylthio, $C_1$–$C_4$-alkylsulphinyl or $C_1$–$C_4$-alkylsulphonyl (which is optionally substituted by fluorine and/or chlorine), di-($C_1$–$C_4$-alkyl)-aminosulphonyl, $C_1$–$C_4$-alkoxy-carbonyl or dimethylaminocarbonyl, and A represents oxygen, sulphur or the grouping $N$—$Z^1$, where
$Z^1$ represents hydrogen, $C_1$–$C_4$-alkyl (which is optionally substituted by fluorine, chlorine, bromine or cyano), $C_3$–$C_6$-cycloalkyl, benzyl, phenyl (which is optionally substituted by fluorine, chlorine, bromine or nitro), $C_1$–$C_4$-alkylcarbonyl, $C_1$–$C_4$-alkoxy-carbonyl or di-($C_1$–$C_4$-alkyl)-aminocarbonyl;

furthermore $R^1$ represents the radical

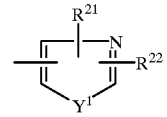

in which
$R^{21}$ and $R^{22}$ are identical or different and each represent hydrogen, $C_1$–$C_4$-alkyl, halogen, $C_1$–$C_4$-alkoxycarbonyl, $C_1$–$C_4$-alkoxy or $C_1$–$C_4$-halogenoalkoxy,
$Y^1$ represents sulphur or the grouping $N$—$R^{23}$, where
$R^{23}$ represents hydrogen or $C_1$–$C_4$-alkyl;

furthermore $R^3$ represents the radical

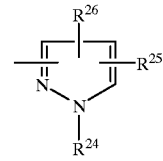

in which
$R^{24}$ represents hydrogen, $C_1$–$C_4$-alkyl, benzyl, pyridyl, quinolyl or phenyl, $R^{25}$ represents hydrogen, halogen, cyano, nitro, $C_1$–$C_4$-alkyl (which is optionally substituted by fluorine and/or chlorine), $C_1$–$C_4$-alkoxy (which is optionally substituted by fluorine and/or chlorine), dioxolanyl or $C_1$–$C_4$-alkoxy-carbonyl and $R^{26}$ represents hydrogen, halogen or $C_1$–$C_4$-alkyl.

Furthermore, the invention preferably provides sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzylammonium salts of the compounds of the formula (I) in which n, $R^1$, $R^2$ and $R^3$ each have the preferred meanings given above.

The invention in particular provides compounds of the formula (I) in which $R^1$ represents respectively optionally fluorine-, chlorine-, cyano-, methoxy- or ethoxy-substituted methyl, ethyl, n- or i-propyl, n-, i-, s- or t-butyl, or respectively optionally fluorine-, chlorine- or bromine-substituted propenyl, butenyl, propinyl or butinyl, or methylamino, ethylamino, n- or i-propylamino, n-, i-, s- or t-butylamino, dimethylamino or diethylamino, or respectively optionally fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or respectively optionally fluorine-, chlorine-, bromine-, cyano-, methyl-, trifluoromethyl- or methoxy-substituted benzyl or phenyl, $R^2$ represents respectively fluorine- and/or chlorine-substituted methyl, ethyl, n- or i-propyl, n-, i-, s- or t-butyl, propenyl or butenyl and $R^3$ represents the radical

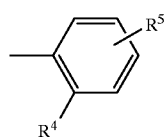

in which $R^4$ represents fluorine, chlorine, bromine, methyl, ethyl, n- or i-propyl, trifluoromethyl, methoxy, ethoxy, n- or i-propoxy, n- or i-butoxy, difluoromethoxy, trifluoromethoxy, 2-chloro-ethoxy, 2,2,2-trifluoro-ethoxy, 1,1,2,2-tetrafluoro-ethoxy, 1,1,2,2,2-pentafluoro-ethoxy, 2-methoxy-ethoxy, methylthio, ethylthio, n- or i-propylthio, n-or i-butylthio, 2-fluoro-ethylthio, allyloxy, propargyloxy, methylsulphinyl, ethylsulphinyl, methylsulphonyl, ethylsulphonyl, dimethylaminosulphonyl, diethylaminosulphonyl, N-methoxy-N-methylamino-sulphonyl, phenyl, phenoxy, methoxycarbonyl, ethoxycarbonyl, n- or i-propoxycarbonyl, and $R^5$ represents hydrogen, methyl, ethyl, fluorine, chlorine or bromine;

furthermore $R^3$ represents the radical

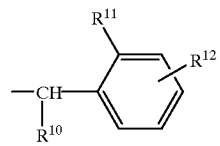

in which $R^{10}$ represents hydrogen, $R^{11}$ represents fluorine, chlorine, bromine, methyl, methoxy, difluoromethoxy, trifluoromethoxy, ethoxy, methoxycarbonyl, ethoxycarbonyl, methyl-sulphonyl or dimethylaminosulphonyl and $R^{12}$ represents hydrogen;

furthermore $R^3$ represents the radical

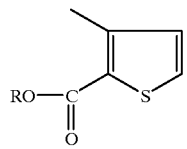

in which

R represents methyl, ethyl, n- or i-propyl, or $R^3$ represents the radical

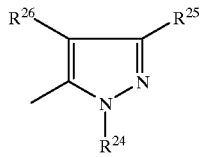

in which $R^{24}$ represents methyl, ethyl, n- or i-propyl, phenyl or pyridyl, $R^{25}$ represents hydrogen, fluorine, chlorine or bromine and $R^{26}$ represents fluorine, chlorine, bromine, methoxy-carbonyl or ethoxycarbonyl.

The abovementioned general or preferred radical definitions apply both to the end products of the formula (I) and, correspondingly, to the precursors or intermediates required in each case for the preparation. These radical definitions can be combined with one another as desired, thus including combination between the preferred ranges indicated.

In the definitions of the radicals, hydrocarbon radicals such as alkyl, alkenyl or alkinyl are straight-chain or branched, even in combinations with hetero atoms, as in alkoxy, alkylthio or alkylamino, even if this is not explicitly stated Halogen generally represents fluorine, chlorine, bromine or iodine, preferably fluorine, chlorine or bromine, in particular fluorine or chlorine.

Using, for example, 2-trifluoromethoxy-phenylsulphonyl isocyanate and 4-ethyl-5-difluoromethylthio-2,4-dihydro-3H-1,2,4-triazol-3-one as starting materials, the course of the reaction in the process (a) according to the invention can be illustrated by the following equation:

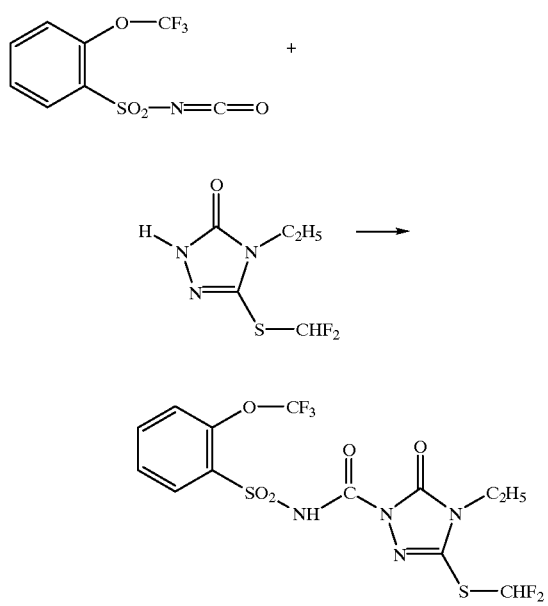

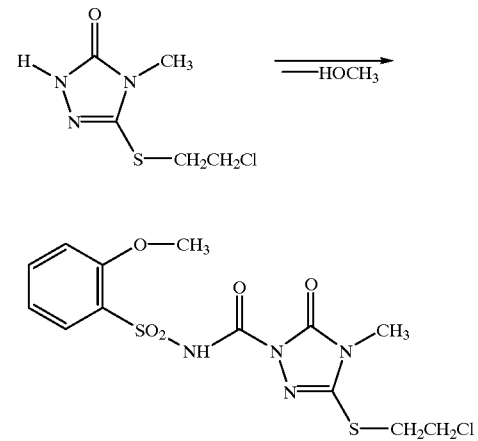

Using, for example, 2-chloro-6-methyl-benzenesulphonyl chloride, 4-allyl-5-(2,3,3-trifluoro-propylthio)-2,4-dihydro-3H-1,2,4-triazol-3-one and sodium cyanate as starting materials, the course of the reaction in the process (d) according to the invention can be illustrated by the following equation:

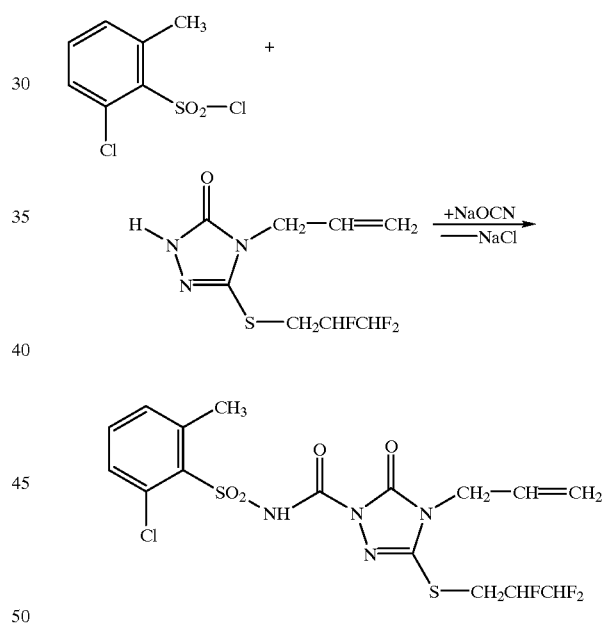

Using, for example, 2-ethylthio-benzenesulphonamide and 2-chlorocarbonyl-4-cyclopropyl-5-(2,2-difluoro-ethylthio)-2,4-dihydro-3H-1,2,4-triazol-3-one as starting materials, the course of the reaction in the process (b) according to the invention can be illustrated by the following equation:

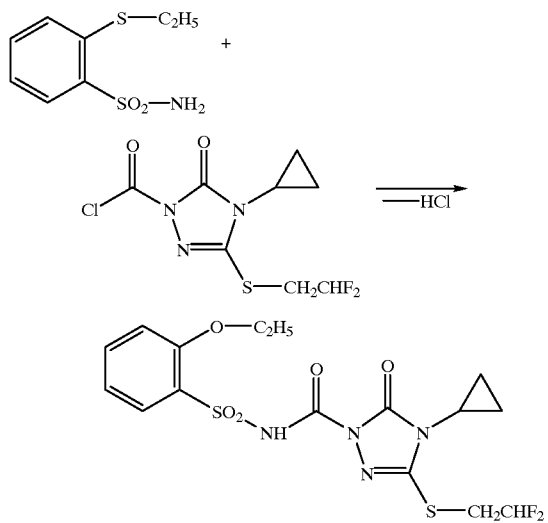

Using, for example, N-methoxycarbonyl-2-methoxy-benzenesulphonamide and 5-(2-chloro-ethylthio)-4-methyl-2,4-dihydro-3H-1,2,4-triazol-3-one as starting materials, the course of the reaction in the process (c) according to the invention can be illustrated by the following equation:

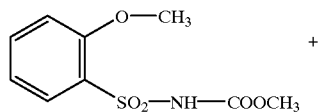

A general definition of the triazolinones to be used as starting materials in the processes (a), (c) and (d) according to the invention for preparing compounds of the formula (I) is given by the formula (II).

In the formula (II), $R^1$ and $R^2$ each preferably or in particular have that meaning which has already been indicated above, in connection with the description of the compounds of the formula (I) according to the invention, as being preferable or particularly preferable for $R^1$ and $R^2$.

The triazolinones of the general formula (II) have not been disclosed in the literature; as novel substances, they also form part of the subject matter of the present application.

The novel triazolinones of the general formula (II) are obtained when mercaptotriazolinones of the general formula (IX)

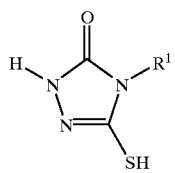

(IX)

in which

R¹ is as defined above

—and/or the corresponding isomeric thiourazoles and/or the corresponding metal salts, in particular sodium salts or potassium salts— are reacted with alkylating agents of the general formula (X)

$$X^1—R^2 \quad (X)$$

in which

R² is as defined above and

X¹ represents halogen, preferably chlorine, bromine or iodine, if appropriate in the presence of an acid acceptor, such as, for example, sodium hydroxide, and in the presence of a diluent, such as, for example dioxane, methanol, ethanol, n- or i-propanol and/or water, at temperatures between 0° C. and 100° C. (cf the preparation examples).

The intermediates of the formula (IX) are known and/or can be prepared by conventional processes (cf EP-A 43 1291; DE-A 2250572; J. Heterocycl. Chem. 15 (1978), 377–384).

The intermediates of the formula (X) are also known and/or can be prepared by conventional processes (cf J. Fluorine Chem. 13 (1979), 325; loc. cit. 20 (1982), 637; loc. cit. 21 (1982), 253; loc. cit 28 (1985), 291); J. Chem. Soc., Perkin II 1975, 1841).

A general definition of the sulphonyl isocyanates also to be used as starting materials in the process (a) according to the invention for preparing compounds of the formula (I) is given by the formula (III).

In the formula (III), R³ preferably or in particular has that meaning which has already been indicated above, in connection with the description of the compounds of the formula (I) according to the invention, as being preferable or particularly preferable for R³.

The starting materials of the formula (III) are known and/or can be prepared by methods known per se (cf. U.S. Pat. No. 4,127,405, U.S. Pat. No. 4,169,719, U.S. Pat. No. 4,371,391, EP-A7687, EP-A 13480, EP-A21641, EP-A23141, EP-A23422, EP-A30139, EP-A 35893; EP-A 44808; EP-A 44809, EP-A 48143, EP-A 51466, EP-A 64322, EP-A 70041, EP-A 173312).

A general definition of the triazolinone derivatives to be used as starting materials in the process (b) according to the invention for preparing compounds of the general formula (I) is given by the formula (IV). In the formula (IV), RI and R² each preferably or in particular have that meaning which has already been indicated above, in connection with the description of the compounds of the formula (I), as being preferable or particularly preferable for R¹ and R²; Z preferably represents fluorine, chlorine, bromine, methoxy, ethoxy, benzyloxy, phenoxy, halogeno- or nitro-phenoxy, and in particular represents methoxy, phenoxy or 4-nitrophenoxy.

The starting materials of the formula (IV) have not been disclosed in the literature; as novel substances, they also form part of the subject matter of the present application.

The novel compounds of the formula (IV) are obtained when triazolinones of the general formula (II)

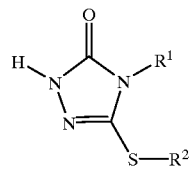

in which

R¹ and R² are each as defined above, are reacted with carbonic acid derivatives of the general formula (XIII)

$$Z—CO—Z^1 \quad (XIII)$$

in which

Z is as defined above and

Z¹ represents halogen, alkoxy, aralkoxy or aryloxy, if appropriate in the presence of an acid acceptor, such as, for example, sodium hydride or potassium hydride, sodium hydroxide or potassium hydroxide, sodium t-butoxide or potassium t-butoxide, and if appropriate in the presence of a diluent, such as, for example, tetrahydrofuran or dimethoxyethane, or in a two-phase system of water and an organic solvent, such as, for example, methylene chloride or chloroform at temperatures between 0° C. and 100° C.

A general definition of the sulphonamides also to be used as starting materials in the process (b) according to the invention for preparing compounds of the general formula (I) is given by the formula (V). In the formula (V), R³ preferably or in particular has that meaning which has already been indicated above, in connection with the description of the compounds of the formula (I), as being preferable or particularly preferable for R³.

The starting materials of the formula (V) are known and/or can be prepared by methods known per se (cf. U.S. Pat. No. 4,127,405, U.S. Pat. No. 4,169,719, U.S. Pat. No. 4,371,391, EP-A 7687, EP-A 13480, EP-A 21641, EP-A 23141, EP-A 23422, EP-A 30139, EP-A 35893, EP-A 44808, EP-A 44809, EP-A 48143, EP-A 51466, EP-A 64322, EP-A 70041, EP-A 173312).

A general definition of the sulphonamide derivatives to be used as starting materials in the process (c) according to the invention for preparing compounds of the formula (I) is given by the formula (VI). In the formula (VI), R³ preferably or in particular has that meaning which has already been indicated above, in connection with the description of the compounds of the formula (I), as being preferable or particularly preferable for R³; Z preferably represents fluorine, chlorine, bromine, methoxy, ethoxy, benzyloxy or phenoxy, and in particular represents methoxy or phenoxy.

The starting materials of the formula (VI) are known and/or can be prepared by methods known per se.

A general definition of the sulphonyl halides to be used as starting materials in the process (d) according to the invention for preparing compounds of the formula (I) is given by the formula (VII). In the formula (VII), R³ preferably or in particular has that meaning which has already been indicated above, in connection with the description of the compounds of the formula (I), as being preferable or particularly preferable for R³; X preferably represents fluorine, chlorine or bromine, and in particular represents chlorine.

The starting materials of the formula (VII) are known and/or can be prepared by methods known per se.

The processes (a), (b), (c) and (d) according to the invention for the preparation of the novel compounds of the formula (I) are preferably carried out using diluents. Suitable diluents in this context are virtually all inert organic solvents. These include, preferably, aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, tetrachloromethane, chlorobenzene and o-dichlorobenzene; ethers such as diethyl ether and dibutyl ether, glycol dimethyl ether and diglycol dimethyl ether, tetrahydrofuran and dioxane; ketones such as acetone, methyl ethyl ketone, methyl isopropyl ketone and methyl isobutyl ketone; esters such as methyl acetate and ethyl acetate; nitriles, for example acetonitrile and propionitrile; amides, for example dimethylformamide, dimethylacetamide and N-methylpyrrolidone, and also dimethyl sulphoxide, tetramethylene sulphone and hexamethylphosphoric triamide.

As reaction auxiliaries and/or as acid acceptors in the processes (a), (b), (c) and (d) according to the invention it is possible to employ all acid-binding agents which can customarily be used for such reactions. Preference is given to alkali metal hydroxides, for example sodium hydroxide and potassium hydroxide, alkaline earth metal hydroxides, for example calcium hydroxide, alkali metal carbonates and alkoxides, such as sodium carbonate and potassium carbonate, sodium tert-butoxide and potassium tert-butoxide, and also basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4,3,0]-non-5-ene (DBN), 1,8-diazabicyclo [5,4,0]-undec-7-ene (DBU) and 1,4-diazabicyclo-[2,2,2]-octane (DABCO).

The reaction temperatures in the processes (a), (b), (c) and (d) according to the invention can be varied within a relatively wide range. The reactions are in general carried out at temperatures of between −20° C. and +100° C., preferably at temperatures between 0° C. and +80° C.

The processes (a), (b), (c) and (d) according to the invention are generally carried out under atmospheric pressure. However, it is also possible to operate under elevated or reduced pressure.

For carrying out processes (a), (b), (c) and (d) according to the invention, the starting materials required in each case are in general employed in approximately equimolar quantities. However, it is also possible to use one of the components employed in each case in a relatively large excess. The reactions are in general carried out in a suitable diluent in the presence of an acid acceptor, and the reaction mixture is stirred for a number of hours at the particular temperature required. Work-up in the case of the processes (a), (b), (c) and (d) according to the invention is in each case carried out by customary methods (cf. the Preparation Examples).

Salts of the compounds of the general formula (I) according to the invention can be prepared if desired. Such salts are obtained in a simple manner by customary methods of forming salts, for example by dissolving or dispersing a compound of the formula (I) in an appropriate solvent, for example methylene chloride, acetone, tert-butyl methyl ether or toluene, and adding an appropriate base. The salts can then—if desired after prolonged stirring—be isolated by concentration or filtration with suction.

The active compounds according to the invention can be used as defoliants, desiccants, haulm killers and, especially, as weed-killers. By weeds, in the broadest sense, there are to be understood all plants which grow in locations where they are not wanted. Whether the substances according to the invention act as total or selective herbicides depends essentially on the amount used.

The active compounds according to the invention can be used, for example, in connection with the following plants: Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial crops, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land. Furthermore, the compounds can be employed for the total control of weeds and for the selective control of weeds in annual crops.

The compounds of the formula (I) according to the invention are particularly suitable for the selective control of monocotyledonous and dicotyledonous weeds in monocotyledonous and dicotyledonous crops, both pre-emergence and post-emergence.

Additionally, the active compounds according to the invention have a potent microbicidal action and can be practically employed for controlling undesirable microorganisms. The active compounds are suitable for use as crop protection agents, in particular as fungicides.

Fungicides in plant protection are employed for controlling Plasmodiophoromycetes, Oomycetes, Chytridiomycetes, Zygomycetes, Ascomycetes, Basidiomycetes and Deuteromycetes.

Bactericides in plant protection are employed for controlling Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation:
Xanthomonas species, such as *Xanthomonas campestris* pv. *oryzae;*
Pseudomonas species, such as *Pseudomonas syringae* pv. *lachrymans;*
Erwinia species, such as *Erwinia amylovora;*
Pythium species, such as *Pythium ultimum;*
Phytophthora species, such as *Phytophthora infestans;*
Pseudoperonospora species, such as *Pseudoperonospora humuli* or *Pseudoperonospora cubensis;*

Plasmopara species, such as *Plasmopara viticola;*
Bremia species, such as *Bremia lactucae;*
Peronospora species, such as *Peronospora pisi* or *P. brassicae;*
Erysiphe species, such as *Erysiphe graminis;*
Sphaerotheca species, such as *Sphaerotheca fuliginea;*
Podosphaera species, such as *Podosphaera leucotricha;*
Venturia species, such as *Venturia inaequalis;*
Pyrenophora species, such as *Pyrenophora teres* or *P. graminea*
(conidia form: Drechslera, syn: Helminthosporium);
Cochliobolus species, such as *Cochliobolus sativus*
(conidia form: Drechslera, syn: Helminthosporium);
Uromyces species, such as *Uromyces appendiculatus;*
Puccinia species, such as *Puccinia recondita;*
Sclerotinia species, such as *Sclerotinia sclerotiorum;*
Tilletia species, such as *Tilletia caries;*
Ustilago species, such as *Ustilago nuda* or *Ustilago avenae;*
Pellicularia species, such as *Pellicularia sasakii;*
Pyricularia species, such as *Pyricularia oryzae;*
Fusarium species, such as *Fusarium culmorum;*
Botrytis species, such as *Botrytis cinerea;*
Septoria species, such as *Septoria nodorum;*
Leptosphaeria species, such as *Leptosphaeria nodorum;*
Cercospora species, such as *Cercospora canescens;*
Alternaria species, such as *Alternaria brassicae;*
Pseudocercosporella species, such as *Pseudocercosporella herpotrichoides.*

The good toleration, by plants, of the active compounds, at the concentrations required for controlling plant diseases, permits treatment of aerial parts of plants, of vegetative propagation stock and seeds, and of the soil.

The compounds of the formula (I) are particularly suitable for the protective treatment of pomaceous fruit, such as apples, against the causative organism of powdery mildew in apple (Podosphaera leucotricha) and to a certain extent also for use in rice against Pyricularia oryzae.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. Suitable liquid solvents are in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are:
for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, ready-to-use formulations or tank mixes being possible.

Possible components for the mixtures are known herbicides, for example anilides, such as diflufenican and propanil; arylcarboxylic acids, such as dichloropicolinic acid, dicamba and picloram; aryloxyalkanoic acids, such as 2,4-D, 2,4-DB, 2,4-DP, fluroxypyr, MCPA, MCPP and triclopyr; aryloxy-phenoxy-alkanoic esters, such as diclofopmethyl, fenoxaprop-ethyl, fluazifop-butyl, haloxyfopmethyl and quizalofop-ethyl; azinones, such as chloridazon and norflurazon; carbamates, such as chlorpropham, desmedipham, phenmedipham and propham; chloroacetanilides, such as alachlor, acetochlor, butachlor, metazachlor, metolachlor, pretilachlor and propachlor; dinitroanilines, such as oryzalin, pendimethalin and trifluralin; diphenyl ethers, such as acifluorfen, bifenox, fluoroglycofen, fomesafen, halosafen, lactofen and oxyfluorfen; ureas, such as chlorotoluron, diuron, fluometuron, isoproturon, linuron and methabenzthiazuron; hydroxylamines, such as alloxydim, clethodim, cycloxydim, sethoxydim and tralkoxydim; imidazolinones, such as imazethapyr, imazamethabenz, imazapyr and imazaquin; nitriles, such as bromoxynil, dichlobenil and ioxynil; oxyacetamides, such as mefenacet; sulphonyl-ureas, such as amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates, such as butylate, cycloate, diallate, EPTC, esprocarb, molinate, prosulfocarb, thiobencarb and triallate; triazines, such as atrazine, cyanazine, simazine, simetryne, terbutryne and terbutylazine; triazinones, such as hexazinone, metamitron and metribuzin; others, such as aminotriazole, benfuresate, bentazone, cinmethylin, clomazone, clopyralid, defenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 2 kg per ha.

The preparation and use of the active compounds according to the invention can be seen from the examples below.

PREPARATION EXAMPLES

Example 1

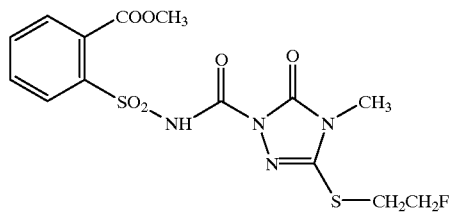

(Process (a))

1.8 g (10 mmol) of 5-(2-fluoro-ethylthio)-4-methyl-2,4-dihydro-3H-1,2,4-triazol-3-one are dissolved in 50 ml of acetonitrile and treated with 2.65 g (11 mmol) of 2-methoxycarbonylphenylsulphonyl isocyanate. The mixture is stirred for 12 hours at 20° C. and then concentrated under reduced pressure. The residue is stirred with isopropanol/petroleum ether (1:1) and crystallized.

3.8 g (91% of theory) of 5-(2-fluoro-ethylthio)-4-methyl-2-(2-methoxy-carbonyl-phenylsulphonyl-aminocarbonyl)-2,4-dihydro-3H-1,2,4-triazol-3-one of melting point 132° C. are obtained.

By the method of Example 1 and in accordance with the general description of the preparation processes according to the invention, it is also possible to prepare, for example, the compounds of the formula (1) listed in Table 1 below.

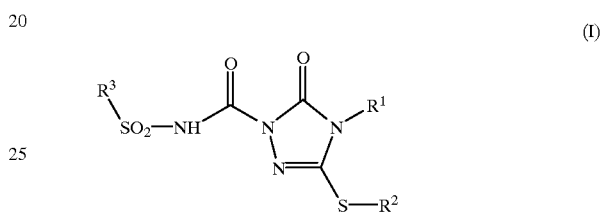

(I)

TABLE 1

| | | Examples of compounds of the formula (I) | | |
|---|---|---|---|---|
| Ex. No. | $R^1$ | $R^2$ | $R^3$ | Melting point (° C.) |
| 2 | $CH_3$ | $CH_2—CH_2—F$ | 2-OCHF$_2$-phenyl | 170 |
| 3 | $CH_3$ | $CH_2—CH_2—F$ | 2-CF$_3$-phenyl | 144 |
| 4 | $CH_3$ | $CH_2—CH_2—F$ | 2-OCF$_3$-phenyl | 130 |
| 5 | $CH_3$ | $CH_2—CH_2—F$ | 2-COOC$_2$H$_5$-phenyl | 133 |
| 6 | $CH_3$ | $CH_2—CH_2—F$ | 2-COOC$_3$H$_7$-phenyl | 151 |

TABLE 1-continued
Examples of compounds of the formula (I)
| Ex. No. | R¹ | R² | R³ | Melting point (° C.) |
|---|---|---|---|---|
| 7 | $CH_3$ | $CH_2-CH_2-F$ | 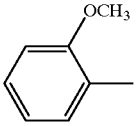 | 171 |
| 8 | $CH_3$ | $CH_2-CH_2-F$ | 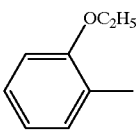 | 159 |
| 9 | $CH_3$ | $CH_2-CH_2-F$ | 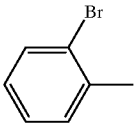 | 137 |
| 10 | $CH_3$ | $CH_2-CH_2-F$ | 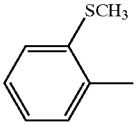 | 158 |
| 11 | $CH_3$ | $CH_2-CH_2-F$ | 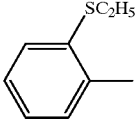 | 149 |
| 12 | $CH_3$ | $CH_2-CH_2-F$ | 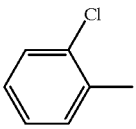 | 153 |
| 13 | $CH_3$ | $CH_2-CH_2-F$ | 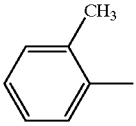 | 134 |
| 14 | $CH_3$ | $CH_2-CH_2-F$ | 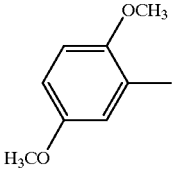 | 181 |
| 15 | $CH_3$ | $CH_2-CH_2-F$ | 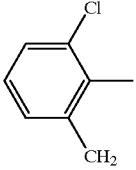 | 121 |

TABLE 1-continued
Examples of compounds of the formula (I)
| Ex. No. | R¹ | R² | R³ | Melting point (° C.) |
|---|---|---|---|---|
| 16 | $CH_3$ | $CH_2-CH_2-F$ | 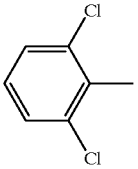 | 143 |
| 17 | $CH_3$ | $CH_2-CF_3$ | 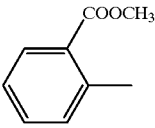 | 133 |
| 18 | $CH_3$ | $CH_2-CF_3$ | 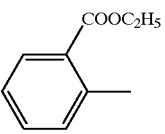 | 147 |
| 19 | $CH_3$ | $CH_2-CF_3$ | 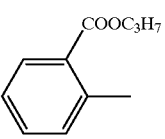 | 156 |
| 20 | $CH_3$ | $CH_2-CF_3$ | 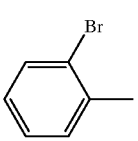 | 153 |
| 21 | $CH_3$ | $CH_2-CF_3$ | 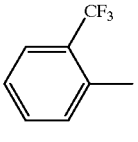 | 157 |
| 22 | $CH_3$ | $CH_2-CF_3$ | 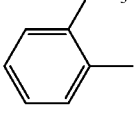 | 141 |
| 23 | $CH_3$ | $CH_2-CF_3$ | 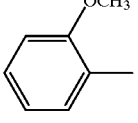 | 99 |
| 24 | $CH_3$ | $CH_2-CF_3$ | 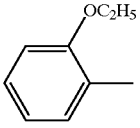 | 116 |

TABLE 1-continued
Examples of compounds of the formula (I)
| Ex. No. | R¹ | R² | R³ | Melting point (° C.) |
|---|---|---|---|---|
| 25 | CH₃ | CH₂—CF₃ | 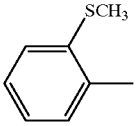 | 112 |
| 26 | CH₃ | CH₂—CF₃ | 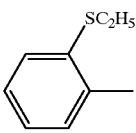 | 111 |
| 27 | CH₃ | CH₂—CF₃ | 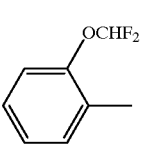 | 89 |
| 28 | CH₃ | CH₂—CF₃ | 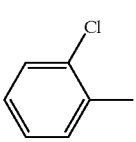 | 147 |
| 29 | CH₃ | CH₂—CF₃ | 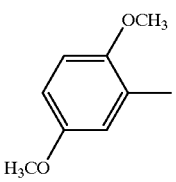 | 149 |
| 30 | CH₃ | CH₂—CF₃ | 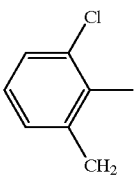 | 130 |
| 31 | CH₃ | CH₂—CF₃ | 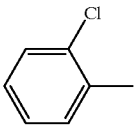 | 169 |
| 32 | CH₃ | CH₂—CH₂—CCl₂—CF₃ | 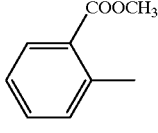 | 151 |
| 33 |  | CH₂—F | 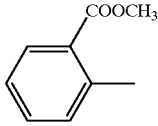 | 140 |

TABLE 1-continued
Examples of compounds of the formula (I)
| Ex. No. | R¹ | R² | R³ | Melting point (° C.) |
|---|---|---|---|---|
| 34 |  | CH₂—Cl | 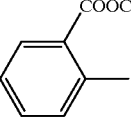 | 152 |
| 35 |  | CH₂—CH₂—F | 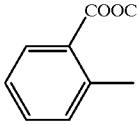 | 164 |
| 36 |  | CH₂—CH₂—F | 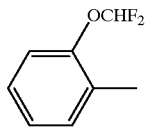 | 126 |
| 37 |  | CH₂—CH₂—F | 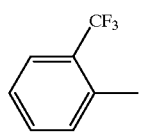 | 143 |
| 38 |  | CH₂—CH₂—F | 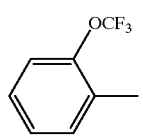 | 130 |
| 39 |  | CH₂—CH₂—F | 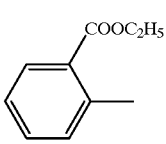 | 141 |
| 40 |  | CH₂—CH₂—F | 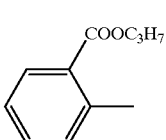 | 134 |
| 41 |  | CH₂—CH₂—F | 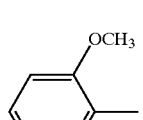 | 154 |
| 42 |  | CH₂—CH₂—F | 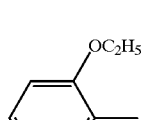 | 177 |
| 43 |  | CH₂—CH₂—F | 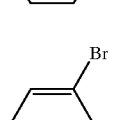 | 138 |

TABLE 1-continued
Examples of compounds of the formula (I)
| Ex. No. | R¹ | R² | R³ | Melting point (° C.) |
|---|---|---|---|---|
| 44 |  | CH₂—CH₂—F | 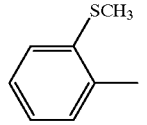 | 161 |
| 45 |  | CH₂—CH₂—F | 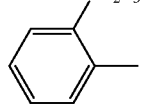 | 125 |
| 46 |  | CH₂—CH₂—F | 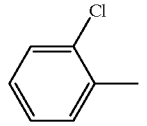 | 106 |
| 47 |  | CH₂—CH₂—F | 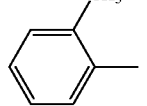 | 121 |
| 48 |  | CH₂—CH₂—F | 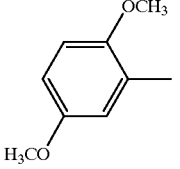 | 133 |
| 49 |  | CH₂—CH₂—F | 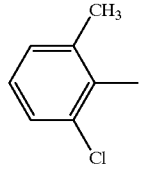 | 155 |
| 50 |  | CH₂—CH₂—F | 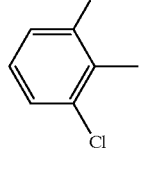 | 147 |
| 51 |  | CH₂—CF₃ | 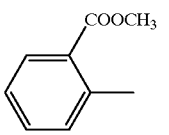 | 144 |
| 52 |  | CH₂—CF₃ | 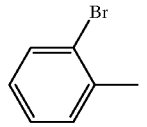 | 95 |

TABLE 1-continued
Examples of compounds of the formula (I)
| Ex. No. | R¹ | R² | R³ | Melting point (° C.) |
|---|---|---|---|---|
| 53 |  | CH₂—CF₃ | 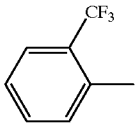 2-CF₃-phenyl | 182 |
| 54 |  | CH₂—CF₃ | 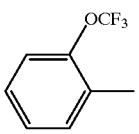 2-OCF₃-phenyl | 152 |
| 55 |  | CH₂—CF₃ | 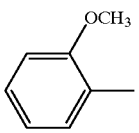 2-OCH₃-phenyl | 115 |
| 56 |  | CH₂—CF₃ | 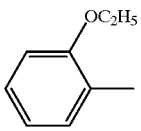 2-OC₂H₅-phenyl | 117 |
| 57 |  | CH₂—CF₃ | 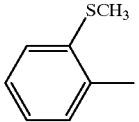 2-SCH₃-phenyl | 146 |
| 58 |  | CH₂—CH₂—F | 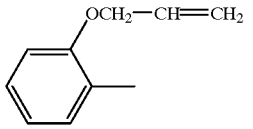 2-OCH₂—CH=CH₂-phenyl | 151 |
| 59 |  | CH₂—CH₂—Cl | 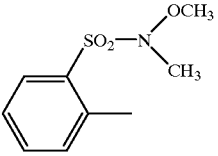 2-SO₂—N(OCH₃)(CH₃)-phenyl | 158 |
| 60 | CH₂—CH=CH₂ | CH₂—CH₂—F | 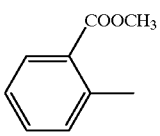 2-COOCH₃-phenyl | 116 |
| 61 | CH₂—CH=CH₂ | CH₂—CH₂—F | 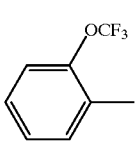 2-OCF₃-phenyl | 104 |
| 62 | CH₂—CH=CH₂ | CH₂—CH₂—F | 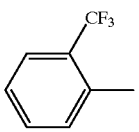 2-CF₃-phenyl | 101 |

TABLE 1-continued

Examples of compounds of the formula (I)

| Ex. No. | R¹ | R² | R³ | Melting point (° C.) |
|---|---|---|---|---|
| 63 | CH₂—CH=CH₂ | CH₂—CH₂—F | 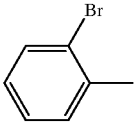 2-Br-phenyl | 108 |
| 64 | CH₂—CH=CH₂ | CH₂—CH₂—F | 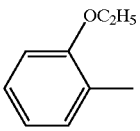 2-OC₂H₅-phenyl | 118 |
| 65 | CH₃ | CH₂—CH₂—CF₃ | 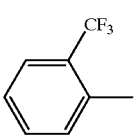 2-CF₃-phenyl | 150 |
| 66 | CH₃ | CH₂—CH₂—CF₃ | 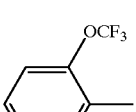 2-OCF₃-phenyl | 111 |
| 67 | CH₃ | CH₂—CH₂—CF₃ | 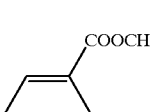 2-COOCH₃-phenyl | 148 |
| 68 | CH₃ | CH₂—CHF₂ | 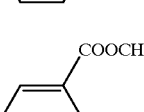 2-COOCH₃-phenyl | 143 |
| 69 | CH₃ | CH₂—CHF₂ | 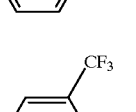 2-CF₃-phenyl | 128 |
| 70 | CH₃ | CH₂—CHF₂ | 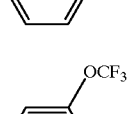 2-OCF₃-phenyl | 136 |
| 71 |  cyclopropyl | CH₂—CH₂—CF₃ | 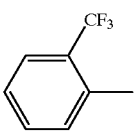 2-CF₃-phenyl | 185 |
| 72 |  cyclopropyl | CH₂—CH₂—CF₃ | 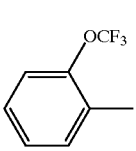 2-OCF₃-phenyl | 166 |

TABLE 1-continued
Examples of compounds of the formula (I)
| Ex. No. | $R^1$ | $R^2$ | $R^3$ | Melting point (° C.) |
|---|---|---|---|---|
| 73 |  | $CH_2-CH_2-CF_3$ | 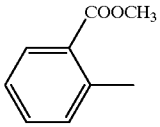 | 165 |
| 74 |  | $CH_2-CHF_2$ | 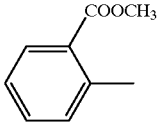 | 169 |
| 75 |  | $CH_2-CHF_2$ | 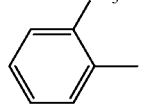 | 154 |
| 76 |  | $CH_2-CHF_2$ | 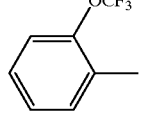 | 138 |
| 77 | $CH_3$ | $CH_2-CH_2-Cl$ | 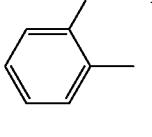 | 165 |
| 78 | $CH_3$ | $CH_2-CH_2-Cl$ | 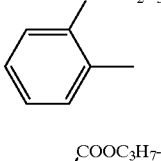 | 146 |
| 79 | $CH_3$ | $CH_2-CH_2-Cl$ | 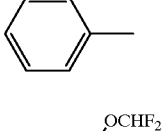 | 145 |
| 80 | $CH_3$ | $CH_2-CH_2-Cl$ | 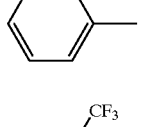 | 139 |
| 81 | $CH_3$ | $CH_2-CH_2-Cl$ | 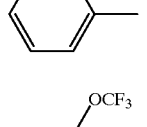 | 135 |
| 82 | $CH_3$ | $CH_2-CH_2-Cl$ | 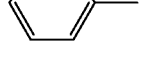 | 121 |

TABLE 1-continued
Examples of compounds of the formula (I)
| Ex. No. | R¹ | R² | R³ | Melting point (° C.) |
|---|---|---|---|---|
| 83 | CH₃ | CH₂—CH₂—Cl | 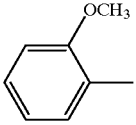 | 179 |
| 84 | CH₃ | CH₂—CH₂—Cl | 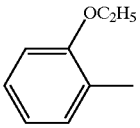 | 178 |
| 85 | CH₃ | CH₂—CH₂—Cl | 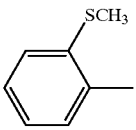 | 171 |
| 86 | CH₃ | CH₂—CH₂—Cl | 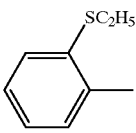 | 132 |
| 87 | CH₃ | CH₂—CH₂—Cl | 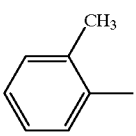 | 130 |
| 88 | CH₃ | CH₂—CH₂—Cl | 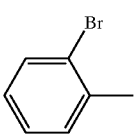 | 140 |
| 89 | CH₃ | CH₂—CH₂—Cl | 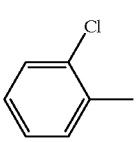 | 139 |
| 90 | CH₃ | CH₂—CH₂—Cl | 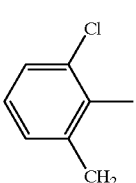 | 127 |
| 91 | CH₃ | CH₂—CH₂—Cl | 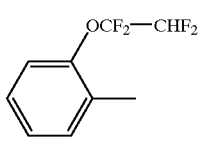 | 123 |

TABLE 1-continued
Examples of compounds of the formula (I)
| Ex. No. | R¹ | R² | R³ | Melting point (° C.) |
|---|---|---|---|---|
| 92 |  | CH₂—CH₂—Cl | 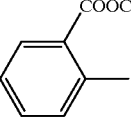 COOCH₃ | 174 |
| 93 |  | CH₂—CH₂—Cl | 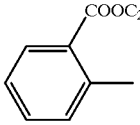 COOC₂H₅ | 132 |
| 94 |  | CH₂—CH₂—Cl | 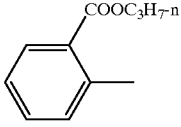 COOC₃H₇-n | 135 |
| 95 |  | CH₂—CH₂—Cl | 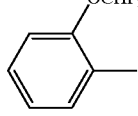 OCHF₂ | 161 |
| 96 |  | CH₂—CH₂—Cl | 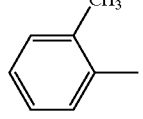 CH₃ | 144 |
| 97 |  | CH₂—CH₂—Cl | 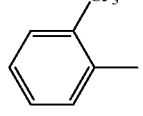 CF₃ | 153 |
| 98 |  | CH₂—CH₂—Cl | 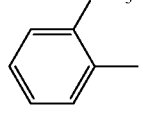 OCF₃ | 140 |
| 99 |  | CH₂—CH₂—Cl | 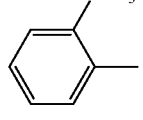 OCH₃ | 167 |
| 100 |  | CH₂—CH₂—Cl | 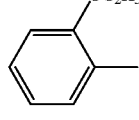 OC₂H₅ | 171 |
| 101 |  | CH₂—CH₂—Cl | 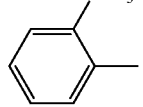 SCH₃ | 180 |

TABLE 1-continued
Examples of compounds of the formula (I)
| Ex. No. | R¹ | R² | R³ | Melting point (° C.) |
|---|---|---|---|---|
| 102 |  | CH₂—CH₂—Cl | 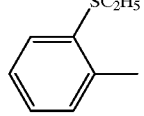 | 152 |
| 103 |  | CH₂—CH₂—Cl | 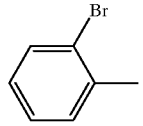 | 123 |
| 104 |  | CH₂—CH₂—Cl | 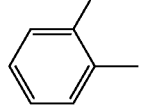 | 124 |
| 105 |  | CH₂—CH₂—Cl | 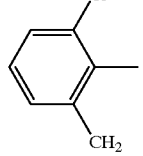 | 172 |
| 106 |  | CH₂—CH₂—Cl | 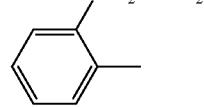 | 132 |
| 107 | CH₃ | CH₂—CH₂—Cl | 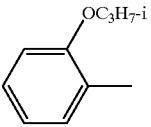 | 147 |
| 108 | CH₃ | CH₂—CH₂—F | 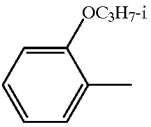 | 153 |
| 109 | CH₃ | CH₂—CF₃ | 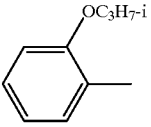 | 147 |
| 110 |  | CH₂—CF₃ | 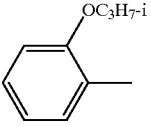 | 128 |

TABLE 1-continued
Examples of compounds of the formula (I)
| Ex. No. | R¹ | R² | R³ | Melting point (° C.) |
|---|---|---|---|---|
| 111 |  | CH₂—CH₂—Cl | 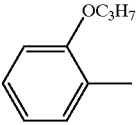 OC₃H₇-i | 129 |
| 112 |  | CH₂—CH₂—F | 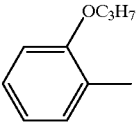 OC₃H₇-i | 146 |
| 113 | CH₃ | CH₂—Cl |  | 164 |
| 114 | CH₃ | CH₂—CH₂—F |  | 138 |
| 115 | CH₃ | CH₂—CH₂—Cl |  | 138 |
| 116 | CH₃ | CH₂—CHF₂ |  | 144 |
| 117 | CH₃ | CH₂—Cl | 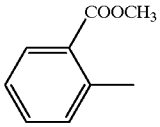 COOCH₃ | 149 |
| 118 | CH₃ | CH₂—Cl | 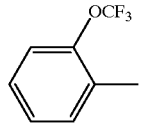 OCF₃ | 181 |
| 119 | CH₃ | CH₂—Cl | 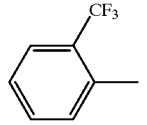 CF₃ | 180 |
| 120 | CH₃ | CH₂—Cl | 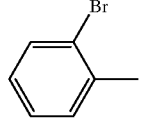 Br | 190 |
| 121 | CH₃ | CH₂—Cl | 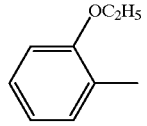 OC₂H₅ | 181 |
| 122 |  | CH₂—Cl | 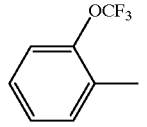 OCF₃ | 129 |

TABLE 1-continued

Examples of compounds of the formula (I)

| Ex. No. | R¹ | R² | R³ | Melting point (° C.) |
|---|---|---|---|---|
| 123 | cyclopropyl | CH₂—Cl | 2-CF₃-phenyl | 157 |
| 124 | cyclopropyl | CH₂—Cl | 2-Br-phenyl | 130 |
| 125 | cyclopropyl | CH₂—Cl | 2-OC₂H₅-phenyl | 169 |
| 126 | cyclopropyl | CH₂—CHF₂ | 2-OC₃H₇-i-phenyl | 158 |
| 127 | CH₃ | CH₂—Cl | 2-OC₃H₇-i-phenyl | 171 |
| 128 | CH₃ | CH₂—CHF₂ | 2-OC₃H₇-i-phenyl | 166 |

The compound listed in Table 1 as Example 58 can, for example, be prepared as follows:

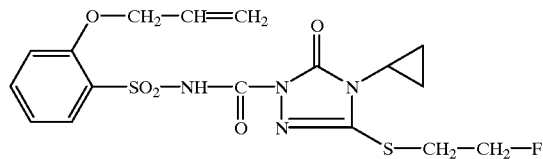

(Process (b))

1.07 g (5 mmol) of 2-allyloxy-benzenesulphonamide are dissolved in 25 ml of acetonitrile and admixed with 0.8 g (5.3 mmol) of diazabicycloundecene (DBU) with stirring. After 30 minutes at 20° C., 1.62 g (5 mmol) of 4-cyclopropyl-5-(2-fluoro-ethylthio)-2-phenoxycarbonyl-2,4-dihydro-3H-1,2,4-triazol-3-one are added and the mixture is stirred for a further 12 hours. The reaction mixture is then poured into ice water, acidified with 10% strength hydrochloric acid and extracted twice with methylene chloride. The residue obtained after drying with magnesium sulphate and concentrating under reduced pressure is crystallized from ether.

1.4 g (63% of theory) of 2-(2-allyloxy-phenylsulphonyl-aminocarbonyl)-4-cyclopropyl-5-(2-fluoro-ethylthio)-2,4-dihydro-3H-1,2,4-triazol-3-one of melting point 151° C. are obtained.

The compound listed in Table 1 as Example 59 can, for example, be prepared as follows

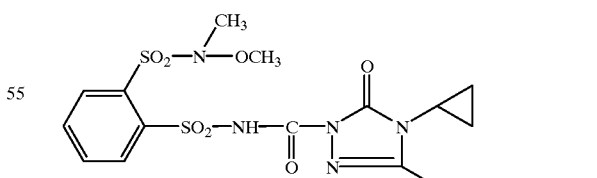

(Process (d))

A mixture of 4.4 g (20 mmol) of 5-(2-chloro-ethylthio)-4-cyclopropyl-2,4-dihydro-3H-1,2,4-triazol-3-one, 7.6 g (24 mmol) of 2-(N-methoxy-N-methyl-aminosulphonyl)-benzene-sulphonyl chloride, 2.6 g (40 mmol) of sodium cyanate and 1.2 g (15 mmol) of pyridine in 50 ml of acetonitrile is stirred at 20° C. for 48 hours. The mixture is then concentrated under reduced pressure and the oily residue is taken up in methylene chloride and washed with 10% strength hydrochloric acid. The organic phase is dried with magnesium sulphate and concentrated under reduced pressure, and the residue obtained is crystallized from methanol/isopropanol.

4.7 g(45% of theory) of 5-(2-chloroethylthio)-4-cyclopropyl-2-[2-N-methoxy-N-methyl-aminosulphonyl)-phenylsulphonyl-aminocarbonyl]-2,4-dihydro-3H-1,2,4-triazol-3-one of melting point 158° C. are obtained.

Starting materials of the formula (II)

Example (II-1)

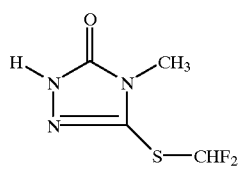

6.6 g (0.05 mol) of 5-mercapto-4-methyl-2,4-dihydro-3H-1,2,4-triazol-3-one are dissolved in 40 ml of water and 40 ml of dioxane and admixed with 10 g (0.25 mol) of sodium hydroxide. With vigorous stirring, a gentle stream of frigen 22 (difluorochloromethane) is passed through the mixture at 80° C. for 16 hours. The solution is allowed to cool, adjusted to a weakly acidic pH using 10% strength hydrochloric acid and then extracted repeatedly with ethyl acetate. The combined organic phases are dried with magnesium sulphate, filtered and concentrated under reduced pressure. The residue is crystallized from diethyl ether.

0.7 g (7.7% of theory) of 5-difluoromethylthio-4-methyl-2,4-dihydro-3H-1,2,4-triazol-3-one of melting point 87° C. is obtained.

Example (II-2)

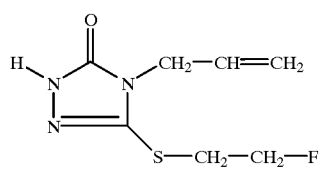

35.1 g (0.18 mol) of the potassium salt of 5-mercapto-4-allyl-2,4-dihydro-3H-1,2,4-triazol-3-one are dissolved in 200 ml of methanol, admixed with 22.9 g (0.18 mol) of 1-bromo-2-fluoro-ethane and stirred at 20° C. for 12 hours. The mixture is then stirred for another 4 hours at 60° C., cooled and concentrated under reduced pressure. The residue is taken up in methylene chloride and washed with 10% strength hydrochloric acid and water. The residue is concentrated under reduced pressure, stirred with petroleum ether and crystallized.

After filtration under suction and drying, 24.8 g (67.9% of theory) of 4-allyl-5-(2-fluoroethylthio)-2,4-dihydro-3H-1,2,4-triazol-3-one of melting point 65° C. are obtained.

By the methods of Examples (II-1) and (II-2), it is also possible to prepare, for example, the compounds of the formula (II) listed in Table 2 below.

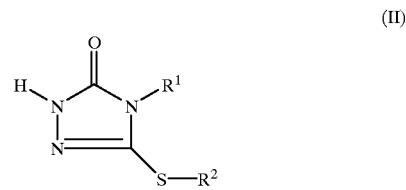

TABLE 2

Examples of compounds of the formula (II)

| Ex. No. | $R^1$ | $R^2$ | Melting point (° C.) |
|---|---|---|---|
| II-3 | $CH_3$ | $CH_2$—$CF_3$ | 132 |
| II-4 | $CH_3$ | $CH_2$—$CH_2$—$CCl_2$—$CF_3$ | 121 |
| II-5 | $CH_3$ | $CH_2$—$CH_2$—F | 88 |
| II-6 | cyclopropyl | $CH_2$—F | 116 |
| II-7 | cyclopropyl | $CH_2$—Cl | 130 |
| II-8 | cyclopropyl | $CH_2$—$CH_2$—F | 120 |
| II-9 | cyclopropyl | $CH_2$—$CF_3$ | 126 |
| II-10 | $CH_3$ | $CH_2$—$CHF_2$ | 95 |
| II-11 | $CH_3$ | $CH_2$—$CH_2$—$CF_3$ | 144 |
| II-12 | cyclopropyl | $CHF_2$ | |
| II-13 | cyclopropyl | $CH_2$—$CHF_2$ | 111 |
| II-14 | cyclopropyl | $CH_2$—$CH_2$—$CF_3$ | 127 |
| II-15 | $CH_3$ | $CH_2$—F | |
| II-16 | $CH_3$ | $CH_2$—Cl | 113 |
| II-17 | cyclopropyl | $CF_3$ | |
| II-18 | $CH_3$ | $CF_3$ | |
| II-19 | $C_2H_5$ | $CF_3$ | |
| II-20 | $CH_2$—CH=$CH_2$ | $CF_3$ | |
| II-21 | $CH_2$—CH=$CH_2$ | $CH_2$—$CHF_2$ | |
| II-22 | $CH_2$—CH=$CH_2$ | $CH_2$—$CF_3$ | |
| II-23 | $CH_2$-cyclopropyl | $CF_3$ | |
| II-24 | $CH_2$-cyclopropyl | $CHF_2$ | |
| II-25 | $CH_2$-cyclopropyl | $CH_2$—F | |

TABLE 2-continued

Examples of compounds of the formula (II)

| Ex. No. | R¹ | R² | Melting point (° C.) |
|---|---|---|---|
| II-26 | CH₂-cyclopropyl | CH₂—CH₂—F | |
| II-27 | CH₂-cyclopropyl | CH₂—CHF₂ | |
| II-28 | CH₂-cyclopropyl | CH₂—CF₃ | |
| II-29 | CH₃ | CH₂—CH₂—Cl | 124 |
| II-30 | CH₂—CH=CH₂ | CH₂—CH₂—Cl | |
| II-31 | cyclopropyl | CH₂—CH₂—Cl | 121 |
| II-32 | CH₂-cyclopropyl | CH₂—CH₂—Cl | |
| II-33 | NH₂ | CH₂—F | |
| II-34 | NH₂ | CH₂—Cl | |
| II-35 | NH₂ | CH—F₂ | |
| II-36 | NH₂ | CF₃ | |
| II-37 | NH₂ | CH₂—CH₂—F | |
| II-38 | NH₂ | CH₂—CH₂—Cl | |
| II-39 | NH₂ | CH₂—CHF₂ | |
| II-40 | NH₂ | CH₂—CF₃ | |
| II-41 | NH—CH₃ | CH₂—F | |
| II-42 | NH—CH₃ | CH₂—Cl | |
| II-43 | NH—CH₃ | CF₃ | |
| II-44 | NH—CH₃ | CH₂—CH₂—F | |
| II-45 | NH—CH₃ | CH₂—CH₂—Cl | |
| II-46 | NH—CH₃ | CH₂—CHF₂ | |
| II-47 | NH—CH₃ | CH₂—CF₃ | |
| II-48 | N(CH₃)₂ | CH₂—F | |
| II-49 | N(CH₃)₂ | CH₂—Cl | |
| II-50 | N(CH₃)₂ | CHF₂ | |
| II-51 | N(CH₃)₂ | CF₃ | |
| II-52 | N(CH₃)₂ | CH₂—CH₂—F | |
| II-53 | N(CH₃)₂ | CH₂—CH₂—Cl | |
| II-54 | N(CH₃)₂ | CH₂—CHF₂ | |
| II-55 | N(CH₃)₂ | CH₂—CF₃ | |
| II-56 | CH₃ | CH₂—CHBr—CF₃ | |
| II-57 | CH₃ | CH₂—CF₂—CHF—CF₃ | ¹H NMR (CDCl₃, δ): 3.28(s, N—CH₃), 3.70 (br, t, S—CH. 4.9–5.2(m, CHF) ppm |
| II-58 | CH₃ | CH₂—CF₂—CHF₂ | ¹H NMR (CDCl₃, δ): 3.28(s, N—CH₃), 3.66(t, S—CH₂, 5.90(tt, CHF₂) ppm |

Starting materials of the formula (IV):

Example (IV-1)

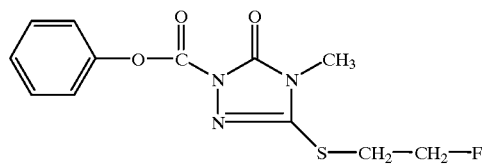

3.44 g (22 mmol) of phenyl chloroformate are added dropwise with efficient stirring to a mixture of 3.54 g (20 mmol) of 5-(2-fluoro-ethylthio)-4-methyl-2,4-dihydro-3H-1,2,4-triazol-3-one, 0.9 g (22 mmol) of sodium-hydroxide, 0.1 g (0.3 mmol) of tetrabutylammonium bromide, 30 ml of water and 40 ml of methylene chloride, and the mixture is stirred for a further 12 hours. The organic phase is separated off, washed with water, dried with magnesium sulphate and concentrated under reduced pressure, and the residue obtained is crystallized from ether.

5.1 g (86% of theory) of 5-(2-fluoro-ethylthio)-4-methyl-2-phenoxy-carbonyl-2,4-dihydro-3H-1,2,4-triazol-3-one of melting point 106° C. are obtained.

By the method of Example (IV-1), it is also possible to prepare, for example, the compounds of the formula (IV) listed in Table 3 below:

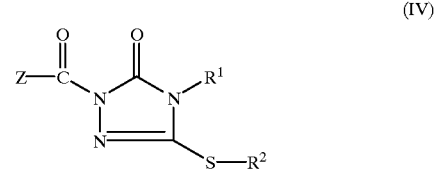

TABLE 3

Examples of compounds of the formula (IV)

| Ex. No. | Z | R¹ | R² | Mp. (° C.) |
|---|---|---|---|---|
| IV-2 | phenyl-O— | cyclopropyl | CH₂—CF₃ | 121 |
| IV-3 | phenyl-O— | cyclopropyl | CH₂—CH₂—F | 129 |

TABLE 3-continued

Examples of compounds of the formula (IV)

| Ex. No. | Z | R¹ | R² | Mp. (° C.) |
|---|---|---|---|---|
| IV-4 | C₆H₅—O— | $CH_3$ | $CH_2-CF_3$ | 114 |
| IV-5 | C₆H₅—O— | $CH_3$ | $CH_2-CHF_2$ | |
| IV-6 | C₆H₅—O— | $CH_3$ | $CH_2-F$ | |
| IV-7 | C₆H₅—O— | $CH_3$ | $CHF_2$ | |
| IV-8 | C₆H₅—O— | cyclopropyl | $CHF_2$ | |
| IV-9 | C₆H₅—O— | cyclopropyl | $CF_3$ | |
| IV-10 | C₆H₅—O— | cyclopropyl | $CH_2-CHF_2$ | |
| IV-11 | C₆H₅—O— | cyclopropyl | $CH_2-CH_2-CF_3$ | |
| IV-12 | C₆H₅—O— | cyclopropyl | $CH_2-CF_2-CHF_2$ | |
| IV-13 | C₆H₅—O— | $CH_3$ | $CF_3$ | |
| IV-14 | C₆H₅—O— | $CH_2-CH=CH_2$ | $CH_2-CH_2-F$ | |
| IV-15 | C₆H₅—O— | $CH_3$ | $CH_2-CH_2-CCl_2-CF_3$ | |
| IV-16 | C₆H₅—O— | cyclopropyl | $CH_2-F$ | |

TABLE 3-continued

Examples of compounds of the formula (IV)

| Ex. No. | Z | R¹ | R² | Mp. (° C.) |
|---|---|---|---|---|
| IV-17 | C₆H₅—O— | cyclopropyl | $CH_2-Cl$ | |
| IV-18 | C₆H₅—O— | $CH_3$ | $CH_2-CH_2-CF_3$ | |
| IV-19 | C₆H₅—O— | $CH_3$ | $CH_2-Cl$ | |
| IV-20 | C₆H₅—O— | $C_2H_5$ | $CF_3$ | |
| IV-21 | C₆H₅—O— | $CH_2-CH=CH_2$ | $CF_3$ | |
| IV-22 | C₆H₅—O— | $CH_2-CH=CH_2$ | $CH_2-CHF_2$ | |
| IV-23 | C₆H₅—O— | $CH_2-CH=CH_2$ | $CH_2-CF_3$ | |
| IV-24 | C₆H₅—O— | $CH_2$-cyclopropyl | $CF_3$ | |
| IV-25 | C₆H₅—O— | $CH_2$-cyclopropyl | $CHF_2$ | |
| IV-26 | C₆H₅—O— | $CH_2$-cyclopropyl | $CH_2F$ | |
| IV-27 | C₆H₅—O— | $CH_2$-cyclopropyl | $CH_2-Cl$ | |
| IV-28 | C₆H₅—O— | $CH_2$-cyclopropyl | $CH_2-CH_2-F$ | |
| IV-29 | C₆H₅—O— | $CH_2$-cyclopropyl | $CH_2-CHF_2$ | |

TABLE 3-continued

Examples of compounds of the formula (IV)

| Ex. No. | Z | R$^1$ | R$^2$ | Mp. (° C.) |
|---|---|---|---|---|
| IV-30 | C$_6$H$_5$—O— | CH$_2$—(cyclopropyl) | CH$_2$—CF$_3$ | |
| IV-31 | C$_6$H$_5$—O— | CH$_2$—(cyclopropyl) | CH$_2$—CH$_2$—Cl | |
| IV-32 | C$_6$H$_5$—O— | CH$_3$ | CH$_2$—CH$_2$—Cl | |
| IV-33 | C$_6$H$_5$—O— | C$_2$H$_5$ | CH$_2$—CH$_2$—Cl | |
| IV-34 | C$_6$H$_5$—O— | cyclopropyl | CH$_2$—CH$_2$—Cl | |
| IV-35 | C$_6$H$_5$—O— | CH$_2$—CH=CH$_2$ | CH$_2$—CH$_2$—Cl | |
| IV-36 | C$_6$H$_5$—O— | NH$_2$ | CH$_2$—F | |
| IV-37 | C$_6$H$_5$—O— | NH$_2$ | CH$_2$—Cl | |
| IV-38 | C$_6$H$_5$—O— | NH$_2$ | CHF$_2$ | |
| IV-39 | C$_6$H$_5$—O— | NH$_2$ | CF$_3$ | |
| IV-40 | C$_6$H$_5$—O— | NH$_2$ | CH$_2$—CH$_2$—F | |
| IV-41 | C$_6$H$_5$—O— | NH$_2$ | CH$_2$—CH$_2$—Cl | |
| IV-42 | C$_6$H$_5$—O— | NH$_2$ | CH$_2$—CHF$_2$ | |

TABLE 3-continued

Examples of compounds of the formula (IV)

| Ex. No. | Z | R¹ | R² | Mp. (° C.) |
|---|---|---|---|---|
| IV-43 | C₆H₅—O— | NH₂ | CH₂—CF₃ | |
| IV-44 | C₆H₅—O— | NH—CH₃ | CH₂—F | |
| IV-45 | C₆H₅—O— | NH—CH₃ | CH₂—Cl | |
| IV-46 | C₆H₅—O— | NH—CH₃ | CHF₂ | |
| IV-47 | C₆H₅—O— | NH—CH₃ | CF₃ | |
| IV-48 | C₆H₅—O— | NH—CH₃ | CH₂—CH₂—F | |
| IV-49 | C₆H₅—O— | NH—CH₃ | CH₂—CH₂—Cl | |
| IV-50 | C₆H₅—O— | NH—CH₃ | CH₂—CHF₂ | |
| IV-51 | C₆H₅—O— | NH—CH₃ | CH₂—CF₃ | |
| IV-52 | C₆H₅—O— | N—(CH₃)₂ | CH₂—F | |
| IV-53 | C₆H₅—O— | N—(CH₃)₂ | CH₂—Cl | |
| IV-54 | C₆H₅—O— | N—(CH₃)₂ | CHF₂ | |
| IV-55 | C₆H₅—O— | N—(CH₃)₂ | CF₃ | |

TABLE 3-continued

Examples of compounds of the formula (IV)

| Ex. No. | Z | R¹ | R² | Mp. (° C.) |
|---|---|---|---|---|
| IV-56 | C₆H₅—O— | N—(CH₃)₂ | CH₂—CH₂—F | |
| IV-57 | C₆H₅—O— | N—(CH₃)₂ | CH₂—CH₂—Cl | |
| IV-58 | C₆H₅—O— | N—(CH₃)₂ | CH₂—CHF₂ | |
| IV-59 | C₆H₅—O— | N—(CH₃)₂ | CH₂—CF₃ | |
| IV-60 | C₆H₅—O— | CH₃ | CH₂—CHBr—CF₃ | |
| IV-61 | C₆H₅—O— | CH₃ | CH₂—CF₂—CHF—CF₃ | |
| IV-62 | C₆H₅—O— | CH₃ | CH₂—CF₂—CHF₂ | |

Use examples:

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, and the stated amount of emulsifier is added and the concentrate is diluted with water to the desired concentration.

Seeds of the test plants are sown in normal soil. After 24 hours, the soil is watered with the preparation of the active compound. It is advantageous to keep constant the amount of water per unit area. The concentration of the active compound in the preparation is not critical, only the amount of active compound applied per unit area being decisive. After 3 weeks, the degree of damage to the plants is rated in per cent damage in comparison to the development of the untreated control. The figures denote:

0%=no action (like untreated control)

100%=total destruction

In this test, the compounds according to Preparation Examples 5, 11, 17, 18, 21, 25, 33, 34, 35, 36, 37, 38, 39, 40, 43, 48, 49, 51, 52, 53, and 54, for example, exhibit a strong action against weeds.

TABLE A

Pre-emergence test/greenhouse

| Compound of Preparation Example No. | Application rate g/ha | Bromus | Poa | Amaranthus | Galinsoga | Matricaria | Portulaca | Viola |
|---|---|---|---|---|---|---|---|---|
| 51 | 250 | 95 | 95 | 95 | 95 | 100 | 95 | 95 |
| 34 | 125 | 80 | 95 | 95 | 95 | 100 | 100 | 90 |
| 52 | 125 | 80 | — | 90 | 95 | 90 | 60 | — |
| 53 | 125 | 90 | — | 90 | 95 | 90 | 80 | 80 |
| 54 | 125 | 90 | — | 90 | 95 | 80 | — | 60 |
| 33 | 125 | 95 | 95 | 95 | 95 | 95 | 95 | 90 |

TABLE A-continued

Pre-emergence test/greenhouse

| Compound of Preparation Example No. | Application rate g/ha | Bromus | Poa | Amaranthus | Galinsoga | Matricaria | Portulaca | Viola |
|---|---|---|---|---|---|---|---|---|
| 17 | 125 | 95 | 95 | 95 | 95 | 95 | 100 | 95 |
| 18 | 125 | 95 | 90 | 80 | 90 | 60 | — | 95 |
| 21 | 125 | 80 | 80 | 90 | 95 | 95 | 90 | 95 |
| 25 | 125 | 95 | 90 | 95 | 95 | 95 | 100 | 90 |
| 5 | 125 | 95 | 95 | 95 | 90 | 80 | 95 | 90 |
| 11 | 125 | 80 | 70 | 95 | 95 | 95 | 95 | 95 |
| 35 | 125 | 95 | 95 | 95 | 95 | 95 | 95 | 95 |
| 36 | 125 | 50 | 80 | 95 | 100 | — | 95 | 90 |
| 37 | 125 | 95 | 60 | 95 | 100 | 95 | 100 | 95 |
| 38 | 125 | 80 | 60 | 95 | 100 | 100 | 90 | 95 |
| 39 | 125 | 95 | 95 | 95 | 95 | 95 | 100 | 95 |
| 40 | 125 | 60 | — | 95 | 95 | 80 | 80 | — |
| 43 | 125 | 80 | 70 | 95 | 100 | 95 | 95 | 95 |
| 48 | 125 | 95 | 95 | 95 | 95 | 95 | 95 | 70 |
| 49 | 125 | 90 | 95 | 95 | 95 | 95 | 80 | 90 |

Example B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular amounts of active compound desired are employed in 2000 l of water/ha. After three weeks, the degree of damage to the plants is rated in % damage in comparison to the development of the untreated control.

The figures denote:

0%=no action (like untreated control)
100%=total destruction

In this test, the compounds of Preparation Examples 5, 8, 10, 11, 17, 33, 34, 38, 39, 48, 49, 51, 52, 53 and 54, for example, show a strong action against weeds.

TABLE B

Post-emergence test/greenhouse

| Compound of Preparation Example No. | Application rate g/ha | Amaranthus | Ambrosia | Helianthus | Matricaria | Solanum | Stellaria | Viola | Xanthium |
|---|---|---|---|---|---|---|---|---|---|
| 51 | 125 | 95 | 90 | 100 | 95 | 95 | 70 | 80 | 95 |
| 34 | 60 | 100 | 95 | 100 | 95 | 100 | 90 | 100 | 100 |
| 52 | 250 | — | 80 | 100 | 90 | 70 | 95 | 60 | 80 |
| 53 | 250 | — | 95 | 100 | 95 | 95 | 95 | 95 | 90 |
| 54 | 125 | 95 | 90 | 100 | 80 | 95 | 70 | 90 | 90 |
| 33 | 60 | 100 | 90 | 100 | 95 | 100 | 95 | 90 | — |
| 17 | 60 | 90 | 90 | 80 | 50 | 80 | 70 | 50 | 90 |
| 5 | 125 | 95 | 90 | 80 | 95 | 95 | 90 | — | 95 |
| 8 | 125 | 100 | 70 | 100 | 95 | 95 | 100 | 100 | 100 |
| 10 | 125 | 100 | — | — | — | 95 | 90 | — | 90 |
| 11 | 125 | 100 | 60 | — | — | 100 | 95 | 60 | 90 |
| 38 | 125 | 95 | 95 | 95 | 70 | 90 | 95 | 95 | 80 |
| 39 | 125 | 100 | 90 | 100 | 95 | 95 | 95 | 95 | 100 |
| 48 | 125 | 95 | 80 | 80 | 80 | 90 | — | 90 | 70 |
| 49 | 125 | 100 | 90 | 100 | 90 | 80 | — | 95 | 70 |

Example C

Podosphaera test (apple)/protective
Solvent: 4.7 parts by weight of acetone
Emulsifier: 0.3 part by weight of allylaryl polyglycol ether To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound. After the spray coating has dried on, the plants are inoculated by dusting with conidiae of the causative organism of apple mildew (*Podosphaera leucotricha*).

The plants are then placed in a greenhouse at 23° C. and a relative atmospheric humidity of about 70%.

Evaluation is carried out 10 days after the inoculation.

In this test, the compounds of Preparation Examples 34 and 51, for example, have an efficacy of 98 to 100% at an active compound concentration of 100 ppm.

TABLE C

Podosphaera test (apple)/protective

| Active compound | Efficacy in % of the untreated control at an active compound concentration of 100 ppm |
|---|---|
| 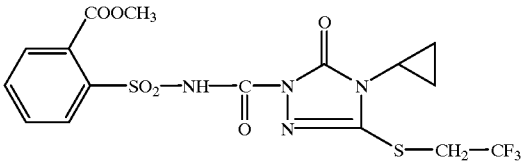 (51) | 98 |
| 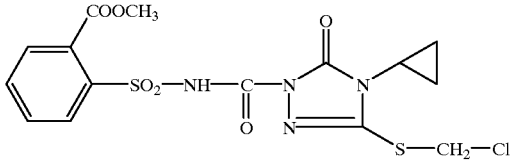 (34) | 100 |

What is claimed is:

1. A compound of the formula (II)

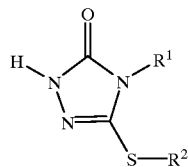

(II)

in which

R$^1$ represents methyl, ethyl, n- or i-propyl, n-, i-, s- or t-butyl, or propenyl, butenyl, or cyclopropyl, cyclobutyl, cyclopentyl, cyclohexyl, R$^2$ represents fluorine- and/or chlorine-substituted methyl, ethyl, n- or i-propyl, n-, i-, s- or t-butyl.

* * * * *